United States Patent [19]

Auger et al.

[11] Patent Number: 5,329,052
[45] Date of Patent: Jul. 12, 1994

[54] PINANES

[75] Inventors: Bernard Auger, Peymeinade, France; Jerzy A. Bajgrowicz, Zurich, Switzerland; Edouard Giraudi, Cruseilles, France

[73] Assignee: Givaudan-Roure Corporation, Clifton, N.J.

[21] Appl. No.: 104,035

[22] PCT Filed: Nov. 28, 1992

[86] PCT No.: PCT/EP92/02754
§ 371 Date: Aug. 5, 1992
§ 102(e) Date: Aug. 5, 1992

[87] PCT Pub. No.: WO93/11094
PCT Pub. Date: Jun. 10, 1993

[30] Foreign Application Priority Data

Dec. 5, 1991 [CH] Switzerland .............. 3571/91
Sep. 11, 1992 [CH] Switzerland .............. 2868/92

[51] Int. Cl.$^5$ .............. C07C 33/05; C07C 33/16; C07C 31/137; A61K 7/46
[52] U.S. Cl. .............. 568/822; 568/826; 568/827; 568/832; 512/215
[58] Field of Search .............. 568/822, 826, 827, 832; 512/8, 25

[56] References Cited

U.S. PATENT DOCUMENTS 4,081,477 3/1978 Hoffmann et al. .
4,424,378 1/1984 Mookherjee et al. .
4,428,387 1/1984 Mookherjee et al. .

FOREIGN PATENT DOCUMENTS 2404306 7/1975 Fed. Rep. of Germany .

Primary Examiner—Werren B. Lone
Attorney, Agent, or Firm—George M. Gould; George W. Johnston

[57] ABSTRACT

The invention relates to novel odorants derived from formylpinane. In particular, these are compounds of the formula

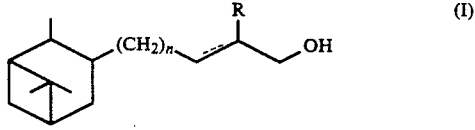

in which R represents H or C—C alkyl, for example methyl, ethyl, propyl, butyl etc., preferably methyl or ethyl, preferably methyl or ethyl, n represents 0 or 1 and the notation $==$ represents a single or double bond I.

14 Claims, No Drawings

PINANES

BACKGROUND

The invention relates to novel odorants derived from formylpinane.

DETAILED DESCRIPTION

In particular, these are compounds of the general formula

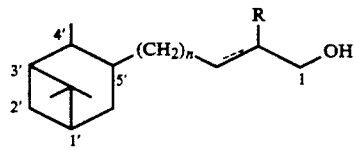

I

The route to these novel compounds I starting from the compounds II is represented in Schemes 1 and 2.

These Schemes also show the preferred routes to the compounds II.

These novel compounds are prepared by reducing a compound of the formula

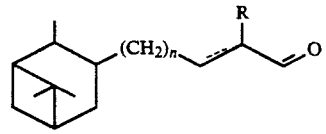

II

Scheme 1

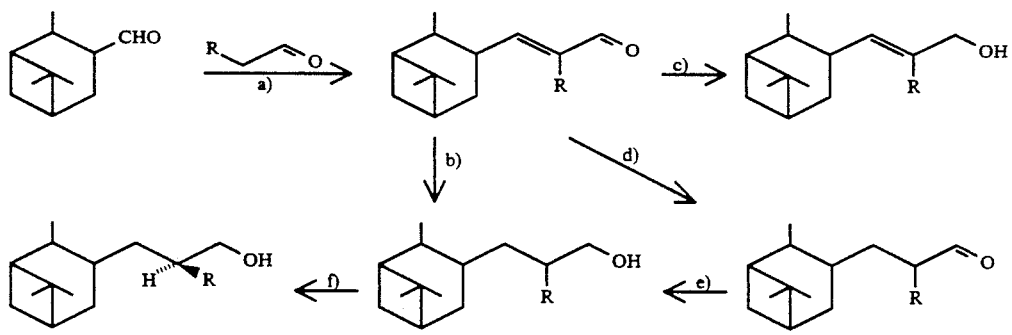

Scheme 2

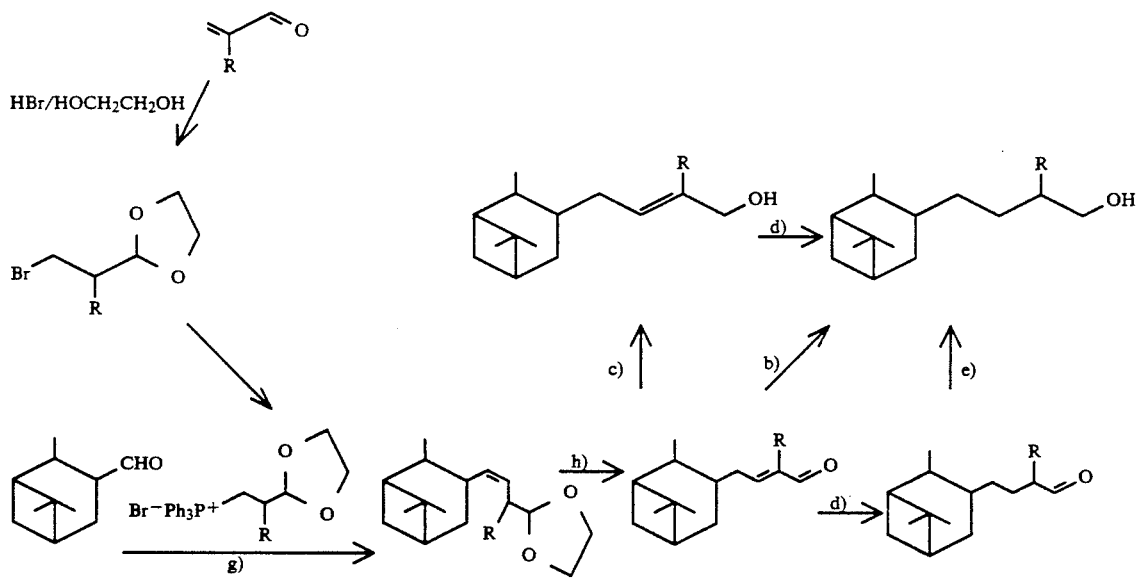

in which R represents H or $C_1$–$C_4$ alkyl, for example methyl, ethyl, propyl, butyl etc., preferably methyl or ethyl, n represents 0 or 1 and the notation ═ represents a single or double bond.

The general formula represents both pure isomers and mixtures of configurational (carbons 2, 1', 3', 4', 5') and geometric double bond of the side chain isomers. In the general formula the configuration of the pinanyl radical depends on that of the formylpinane used in the synthesis.

One possible route to the compounds I is represented in Schemes 1 and 2 and comprises one of the following conversions:

a) aldol condensation of the aldehydes with formylpinane;
b) catalytic hydrogenation of the two unsaturated bonds;
c) selective reduction of carbonyl;
d) selective hydrogenation of the "C═C" bond;
e) reduction of carbonyl;

f) separation of diastereoisomers;
g) Wittig olefination of formylpinane using a phosphonium halide derived from e.g. 3-bromo-2-methylpropanal, protected in the dioxolane form, and from a phosphine, e.g. PPh$_3$;
h) deprotection of the carbonyl functional accompanied by migration of the "C=C" double bond.

The reactions and separation techniques are known per se, namely:
a) aldol condensation catalyzed with strong bases, e.g. metal hydroxides or organic bases;
c) selective reduction of carbonyl in the presence of a "C=C" bond using metal hydrides, e.g. LiAlH$_4$, NaBH$_4$; see also process e);
d) hydrogenation in the presence of noble metal-based catalysts e.g. palladium on charcoal, carried out at atmospheric pressure (→d)) or above, e.g. up to approximately 30 atm. or more (→b));
e) the reaction conditions are analogous to those in c);
f) separation of diastereoisomers by, for example, flash chromatography or another physico-chemical method, e.g. fractionation under reduced pressure;
g) Wittig reaction using phosphoranes generated from a phosphonium halide with a strong base, e.g. butyllithium, in a solvent, for example an ether such as THF;
h) hydrolysis of a 1,3-dioxolane catalyzed with an acid e.g. hydrochloric acid, accompanied by the migration of a carbon-carbon double bond ending in an $\alpha,\beta$-unsaturated system; the solvent is, for example, an ether, preferably THF.

The details of these methods are given in the Examples. It will be understood that modifications concerning the reactants and the reaction conditions are possible and are an integral part of the invention.

The compounds of formula I can be isolated by extracting the reaction mixture (separated from the catalyst or hydrolyzed), with an organic solvent, preferably ethyl ether, methylene chloride or toluene and the like.

The residue can be purified by fractional distillation or flash chromatography.

Formylpinane can be efficaciously prepared starting from α-pinene. The enantiomerically pure forms of this compound can be obtained depending on whether (−)-α-pinene or (+)-α-pinene is used as the starting material (DE 2,404,306 of 31.7.1975) and can be used individually or as a mixture:

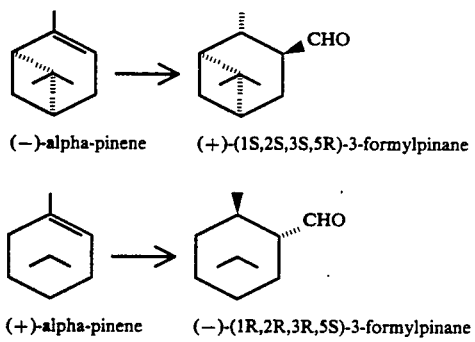

(−)-alpha-pinene  (+)-(1S,2S,3S,5R)-3-formylpinane (+)-alpha-pinene  (−)-(1R,2R,3R,5S)-3-formylpinane It has been found that the compounds I have advantageous olfactory properties and can be used as perfume ingredients. This use in perfumery is also an object of the invention.

The olfactory notes of the aforementioned compounds are woody with an amber and sandalwood tonality.

The present invention also relates to the use of the said compounds, separately or as a mixture, as perfume ingredients for the preparation of perfumes or scented products.

These derivatives of formylpinanes have a woody note with an amber tonality which is extremely advantageous for use in perfumery. As modern perfumery imposes all kinds of constraints, especially as regards eliminating the use of amber notes of animal origin, such as ambergris, it is very important to search for synthetic products with a similar effect in harmony with other families of notes which are widely used, such as the woody ones.

This is the case with these derivatives which combine, according to the individual structure, a more or less woody or amber effect.

Their olfactory value makes it possible for them to harmonize with the majority of natural or synthetic products already widely used in compositions principally for the middle and bottom notes, since these derivatives are endowed with an excellent tenacity (several days on a "blotter" and in various bases).

These derivatives harmonize particularly well with all the floral notes and principally jasmin, rose, narcissus, iris and ylang-ylang. They also harmonize with balsamic or resinous end notes such as styrax, incense and benzoin, and woody notes such as oak moss or tree moss, patchouli and vetiver.

They form very harmonious mixtures in the presence of synthetic products, principally with products containing an alcohol group (geraniol, citronellol, linalool, phenethyl alcohol or cinnamic alcohol), a ketone group, such as the ionones and methylionones, an ester group with a rosy or jasmin or green odour, or a lactone group, such as Hibiscolide and Exaltolide, and also with the macrocyclic polycyclic indane and nitro musks.

The percentage in which these derivatives are used may vary within fairly wide limits ranging from a few parts per thousand in mass market cleaning products up to a few percent (1 to 7 or 8%) in alcoholic extracts for couture perfumery. Overdoses of up to 20% of these derivatives have also been investigated, and these alternate very particular effects in combination with synthetic musks. Such amounts must not be interpreted in a restrictive manner, because they depend on the nature of the product to be perfumed, on the other compounds present in the composition and on the effect which it is desired to obtain.

There is no restriction regarding the type of formulations and the destinations of the finished product, eau de cologne, toilet water, scented water, perfume, cream, shampoo, deodorant, soap, detergent powder, household cleaner, softener, etc.

The formylpinane derivatives are perfectly integrated into oriental chypres, green and woody florals, floral leathers, fougère tobaccos and fruity aldehydes. They give, via their olfactory note, an exceptional richness and linkage between the bottom constituents of the compositions by providing more warmth, velvetiness, depth and persistence.

EXAMPLE 1

(E/Z)-2-Methyl-3-[(1S,2R,3S,5S)-3-pinanyl]-2-propenal 216 g (1.3 mol) of (+)-(1S,2S,3S,5R)-3-formylpinane 166 ml of methanol and 48 g of a 30% sodium hydroxide solution (0.3 mol) are charged into a 2 reactor equipped with a mechanical stirrer, a condenser, a dropping funnel and a device for introducing nitrogen. The mixture is heated to 45°-50° C. and then 302 g (5.2 mol) of propanal are introduced within 30 minutes while maintaining the temperature at approximately 50° C. (cold water bsath). The reaction mixture is maintained for a further 30 minutes at 45° C. and is then cooled and poured into 600 ml of water. After extraction with 3×200 ml of petroleum ether the combined organic phases are washed neutral with sodium chloride solution and dried ($Na_2SO_4$). Evaporation of the solvent followed by fractionation under nitrogen and under vacuum gives 148 g of (E/Z)-2-methyl-3-[(1S,2R,3S,5S)-3-pinanyl]-2-propenal (yield 55%).

B.p.$_{0.4}$=77°-87° C.

IR (film): 1000, 1023, 1380, 1455, 1641, 1686, 2920 $cm^{-1}$.

$^1H$ NMR (200 MHz; $CDCl_3$): 0.8–1.25 (m, 10H); 1.76 (d, J=1.4, 3H); 1.25–3.1 (m, 7H); 6.35 (d, J=10, 0.5H); 6.52 (d, J=10, 0.5H); 9.40 (s, 0.5H); 9.42 (s, 0.5H).

The nomenclature used in the Examples follows the rules of Cahn, Ingold and Prelog.

EXAMPLE 2

(R/S)-2-Methyl-3-[(1S,2R,3R,5S)-3-pinanyl]-1-propanol 113 g (0.55 mol) of (E/Z)-2-methyl-3-[(1S,2R,3S,5S)-3-pinanyl]-2-propenal and 1.13 g of Raney-nickel are charged into a 500 ml autoclave. The autoclave is heated for 20 h. at 150° C. under 150 atm. of hydrogen. After cooling and removal of the catalyst by filtration the reaction mixture is distilled at 0.2 mm Hg to give 83 g of (R/S)-2-methyl-3-[(1S,2R,3R,5S)-3-pinanyl]-1-propanol (yield=72%).

B.p.$_{0.2}$=75°-80° C.

IR (film): 1035, 1373, 1383, 1455, 1471, 2903, 3338 $cm^{-1}$.

$^1H$ NMR (200 MHz; $CDCl_3$): 0.8 (d, J=9, 1H); 0.9–1.22 (m, 12H); 1.25–2.35 (m, 11H); 3.3 (m, 2H).

Analysis by gas chromatography on an apparatus equipped with a Chiraldex BPH (ASTEC) column (length 25 m; internal diameter 0.25 mm) operating at an isothermic temperature of 90° C. using helium as the vector gas at 0.7 ml/min. shows the presence of two peaks having retention times of 61.50 and 68.02 min.

Odour: woody, amber-like, lactonic and sandalwood note.

EXAMPLE 3

(E/Z)-2-Methyl-3-[(1S,2R,3S,5S)-3-pinanyl]-2-propen-1-ol

To a suspension of 3.9 g (0.10 mol) of sodium borohydride in 4 ml of absolute ethanol cooled to 0° C. are added 15 g (73 mmol) of (E/Z)-2-methyl-3-[(1S.2R,3S,5S)-3-pinanyl]-2-propenal during 75 min. while maintaining the temperature at ≦5° C. Stirring of the mixture is continued at this temperature for 1 h., then 120 ml of water are added and the mixture is extracted with 3×50 ml of ethyl ether. The combined organic phases are washed with 3×20 ml of water, dried ($MgSO_4$) and concentrated under vacuum. The residue is purified by distillation at 0.2 mm Hg: 12.4 g of (E/Z)-2-methyl-3-[(1S,2R,3S,5S)-3-pinanyl]-3-pinanyl]-2-propen-1-ol (yield=82%).

B.p.$_{0.2}$=85°-86° C.

IR (film): 730, 910, 1010, 1360, 1440, 1615, 2900, 3300 $cm^{-1}$.

$^1H$ NMR (200 MHz; $CDCl_3$): 0.76 (d, J=10, 1H); 0.95 (d, J=7, 3H); 1.08 (s, 3H); 1.20 (s, 3H); 1.48 (ddd, J=15,7,2,1H); 1.7 (s, 3H); 1.75 (m, 2H); 1.9 (m, 1H); 2.18 (m, 1H); 2.32 (m, 1H); 2.65 (m, 1H); 4.0 (s, 2H); 5.3 (d, J=10, 1H).

Odour: amber-like, coniferous, eucalyptus.

EXAMPLE 4

(E/Z)-2-Ethyl-3-[(1S,2R,3S,5S)-3-pinanyl]-2-propenal 13.5 g (0.20 mol) of 85% KOH pellets, 225 ml of methanol and 249 g 1.5 mol of (+)-(1S,2S,3S,5R)-3-formylpinane are changed to a 1 l round-bottomed flask equipped with a mechanical stirrer, a dropping funnel, a condenser and a device for introducing nitrogen. The mixture is heated at 60° C. and 432 g of butanal are added over 1 hour at this temperature. The mixture is maintained for a further 30 minutes at 60° C. and then poured into 750 ml of water, separated and extracted with 2×150 ml of petroleum ether. The organic phases are washed with 2×100 ml of water and dried over $MgSO_4$. After evaporation of the solvent under vacuum and fractionation at 0.5 Hg there are obtained 148 g of (E/Z)-2-ethyl-3-[(1S,2R,3S,5S)-3-pinanyl]-2-propenal (yield 45%).

B.p.$_{0.5}$=82°-92° C.

$n^{20}$=1.4997

IR (film): 785, 1151, 1372, 1457, 1640, 1687, 2915 $cm^{-1}$.

$^1H$ NMR (200 MHz; $CDCl_3$): 0.85 (d, J=9, 1H); 0.97 (t, J=7.5, 3H); 0.99 (d, J=7.5, 3H); 1.09 (s, 3H); 1.22 (s, 3H); 1.5–3.1 (m, 9H); 6.28 (d, J=10, 1H); 9.36 (s, 1H).

EXAMPLE 5

(R/S)-2-Ethyl-3-[(1S,2R,3R,5S)-3-pinanyl]-1-propanol

Under the same conditions as those in Example 2, starting from 145 g (0.586 mol) of (E/Z)-2-ethyl-3-[(1S,2R,3S,5S)-3-pinanyl]-2-propenal and 1.45 g of Raney-nickel there are obtained 108 g of (R/S)-2-ethyl-3-[(1S,2R,3R,5S)-3-pinanyl]-1-propanol. obtained (yield 82%).

B.p.$_{0.5}$=95°-97° C.

$n^{20}$=1.4843.

IR (film): 1030, 1367, 1440, 2880, 3320 $cm^{-1}$.

$^1H$ NMR (200 MHz; $CDCl_3$): 0.75 (d, J=9, 1H); 0.8–2.4 (m, 22H); 1.19 (s, 3H); 3.4–3.7 (m, 2H).

Chiral gas-chromatographic analysis carried out under the same conditions as those of Example 2 except for the temperature (100° C.) shows the presence of two peaks having retention times of 51.86 and 55.83 min.

Odour: amber-like bottom note, tenacious.

EXAMPLE 6

(E/Z)-2-Ethyl-3-[(1S,2R,3S,5S)-3-pinanyl]-2-propen-1-ol

Under the same conditions as those in Example 3, starting from 12.1 g (55 mmol) of (E/Z)-2-ethyl-3-[(1S,2R,3S,5S)-3-pinanyl]-2-propenal there are obtained 9.6 g of (E/Z)-2-ethyl-3-[(1S,2R,3S,5S)-3-pinanyl]-2-propen-1-ol (yield 79%).

B.p.$_{0.3}$=97°–98° C.

IR (film): 780, 875, 1020, 1380, 1460, 2900, 3300 cm$^{-1}$.

$^1$H NMR (200 MHz; CDCl$_3$): 0.76 (d, J=10, 1H); 0.94 (d, J=7, 3H); 0.98 (t, J=7, 3H); 1.04 (s, 3H); 1.16 (s, 3H); 1.47 (ddd, J=15,7,2,1H); 1.6–2.42 (m, 7H); 2.62 (m, 1H); 4.0 (s, 2H); 5.21 (d, J=10, 1H).

Odour: amber-like, woody, eucalyptus.

EXAMPLE 7

[2-(1,3-Dioxolan-2-yl)propan-1-yl]triphenylphosphonium bromide

A mixture of 110 g (0.56 mol) of 2-(1-bromopropan-2-yl)-1,3-dioxolane, 148.5 g (0.56 mol) of triphenylphosphine and 550 ml of anhydrous toluene is heated at reflux under nitrogen for 24 h. The paste-like salt phase is separated and washed with 5×200 ml of anhydrous ethyl ether. After drying under vacuum there are obtained 191 g of [2-(1,3-dioxolan-2-yl)propan-1-yl]triphenylphosphonium bromide (white solid; yield 75%).

IR (KBr): 692, 722, 751, 1112, 1439, 2884 cm$^{-1}$.

$^1$H NMR (200 MHz; CDCl$_3$): 0.92 (d, J=7, 3H); 2.19 (m, 1H); 3.3–4.2 (m, 6H); 4.8 (d, J=3.5, 1H); 7.55–7.95 (m, 15H).

EXAMPLE 8

(Z)-2-[4-[(1S,2R,3S,5S)-3-Pinanyl]but-3-en-2-yl]-1,3-dioxolane 100 g (0.219 mol) of the phosphonium salt from Example 7 and 940 ml of anhydrous THF are charged under argon into a 2.5 l three-necked flask equipped with a dropping funnel and a mechanical stirrer. The suspension is cooled to −30° C. and 137 ml (0.219 mol) of butyllithium solution (1.6M in hexane) are added dropwise at this temperature. After 1 h. at −30° C. a solution of 24.2 g (0.146 mol) of (+)-(1S,2S,3S,5R)-3-formylpinane in 526 ml of anhydrous THF is added over 1 h. Stirring is maintained for 1 h. at −30° C. and then the reaction mixture is poured into 1 l of ice-cold water. After extraction with 3×500 ml of ethyl ether, drying (MgSO$_4$) and evaporation of the solvents under vacuum there are obtained 54 g of an oil which is purified by flash chromatography on silica (eluent: petroleum ether+1% ethyl ether) to give 21 g of (Z)-2-[4-[(1S,2R,3S,5S)-3-pinanyl]but-3-en-2-yl]-1,3-dioxolane (yield=55%).

IR (film): 754, 943, 1066, 1101, 1152, 1371, 1386, 1455, 1472, 2901 cm$^{-1}$.

$^1$H NMR (200 MHz; CDCl$_3$): 0.77 (d, J=9, 1H); 0.9–1.1 (m, 9H); 1.2 (s, 3H); 1.4–2.9 (m, 8H); 3.75–4.05 (m, 4H); 4.69 (d, J=4.5, 0.5H); 4.71 (d, J=4.5, 0.5H); 5.09–5.42 (m, 2H).

EXAMPLE 9

(E)-2-Methyl-4-[(1S,2R,3S,5S)-3-pinanyl]-2-butenal

A mixture of 18.1 g (68.6 mmol) of the dioxolane of Example 8, 250 ml of THF and 120 ml of 4N HCl is stirred for 4 days at room temperature (monitoring by gas chromatography) and is then poured into 250 ml of ice-cold water. After extraction with 3×200 ml of ethyl ether, drying (MgSO$_4$) and evaporation of the solvents there are obtained 19 g of crude oil which is purified by flash chromatography on silica (eluent: petroleum ether+1% ethyl ether) to give 10.5 g of (E)-2-methyl-4-[(1S,2R,3S,5S)-3-pinanyl]-2-butenal (yield=70%).

IR (film): 999, 1382, 1454, 1472, 1645, 1690, 2906 cm$^{-1}$.

$^1$H NMR (200 MHz; CDCl$_3$): 0.77 (d, J=9, 1H); 1.0 (s, 3H); 1.03 (d, J=7.5, 3H); 1.18 (s, 3H); 1.4–2.65 (m, 9H); 1.76 (br s, 3H); 6.56 (br t, J=7.5, 1H); 9.41 (s, 1H).

EXAMPLE 10

(E)-2-Methyl-4-[(1S,2R,3S,5S)-3-pinanyl]-2-buten-1-ol 20.4 ml (20 mmol) of a 1M solution of LiAlH$_4$ in ethyl ether and 20 ml of anhydrous ethyl ether are charged under a stream of nitrogen into a 100 ml reactor equipped with a mechanical stirrer and a condenser. 4.5 g (20 mmol) of (E)-2-methyl-4-[(1S,2R,3S,5S)-3-pinanyl]-2-butenal are added dropwise and the mixture is heated at reflux for 4 h. After cooling the mixture to 10° C. 25 ml of water are added, the suspension is stirred for 30 minutes and extracted with 3×100 ml of ethyl ether. After drying (MgSO$_4$), evaporation of the solvents under a vacuum and flash chromatography (SiO$_2$/petroleum ether+1% ethyl ether) there is obtained an oil which, after bulb-tube (Kugelrohr) distillation, gives 3.91 g of (E)-2-methyl-4-[(1S,2R,3S,5S)-3-pinanyl]-2-buten-1-ol (yield=87%).

IR (film): 1011, 1371, 1384, 1453, 1471, 2904, 3320 cm$^{-1}$.

$^1$H NMR (200 MHz; CDCl$_3$): 0.75 (d, J=9, 1H); 0.98 (s, 3H); 1.0 (d, J=7.5, 3H); 1.17 (s, 3H); 1.35–2.4 (m, 10H); 1.68 (br s, 3H); 4.0 (br s, 2H); 5.47 (br t, J=7.5, 1H).

Odour: woody, sandalwood and slightly lactonic note with a fresh amber tendency.

EXAMPLE 11

(R/S)-2-Methyl-4-[(1S,2R,3S,5S)-3-pinanyl]butanal

A mixture of 12.0 g (55 mmol) of (E)-2-methyl-4-[(1S,2R,3S,5S)-3-pinanyl]-2-butenal, 100 ml of hexane and 0.36 g of 5% palladium on charcoal is hydrogenated for 3 h. at atmospheric pressure. After filtration of the catalyst and evaporation of the solvent under vacuum there are obtained 12.2 g of (R/S)-2-methyl-4-[(1S,2R,3S,5S)-3-pinanyl]butanal (yield=100%).

IR (film): 1239, 1375, 1384, 1456, 1469, 1707, 1727, 2916 cm$^{-1}$.

$^1$H NMR (200 MHz; CDCl$_3$): 0.72 (d, J=9, 1H); 0.95–2.55 (m, 18H); 0.98 (s, 3H); 1.17 (s, 3H); 9.61 (d, J=2, 0.5H); 9.62 (d, J=2, 0.5H).

EXAMPLE 12

(R/S)-2-Methyl-4-[(1S,2R,3S,5S)-3-pinanyl]-1-butanol 7.9 ml (7.9 mmol) of 1M LiAlH$_4$ solution in ethyl ether and 6 ml of anhydrous ethyl ether are charged under nitrogen into a 25 ml three-necked flask equipped with a thermometer, a condenser and a magnetic stirrer and 3.5 g (15.7 mmol) of (R/S)-2-methyl-4-[(1S,2R,3S,5S)-3-pinanyl]butanal diluted in 6 ml of the same solvent are then added. The mixture is heated at reflux for 2 h. and is then cooled to 10° C. 0.3 ml of water, 0.3 ml of 15% aqueous NaOH solution and 0.8 ml of water are added successively and stirring is maintained for 10 minutes. After filteration through kieselguhr and evaporation of the ether phase the residue is purified by flash chromatography on silica (eluent: petroleum ether/ethyl ether 93:7) and distilled in a bulb-tube (Kugelrohr) to give 2.85 g of (R/S)-2-methyl-4-[(1S,2R,3S,5S)-3-pinanyl]-1-butanol (yield 81%).

IR (film): 1038, 1372, 1383, 1454, 1471, 2916m 3330 cm$^{-1}$.

$^1$H NMR (200 MHz; CDCl$_3$): 0.72 (d, J=9, 1H); 0.91 (d, J=7.5, 1.5H); 0.93 (d, J=7.5, 1.5H); 0.98 (s, 3H); 1.0 (d, J=7, 3H); 1.05–2.40 (m, 13H); 1.17 (s, 3H); 3.34–3.62 (m, 2H).

Odour: sandalwood note, a very slight heavy tobacco note in the bottom, faintly amber-like.

EXAMPLE 13

(R/S)-2-Methyl-3-[(1R,2S,3S,5R)-3-pinanyl]-1-propanol

Under the same conditions as those in Examples 1 and 2, starting from 5.0 g (30 mmol) of (−)-(1R,2R,3R,5S)-3-formylpinane there are obtained 1.4 g of (R/S)-2-methyl-3-[(1R,2S,3S,5R)-3-pinanyl]-1-propanol (overall yield 22%). Physical properties: IR and $^1$H NMR are identical with those of (R/S)-2-methyl-3-[(1S,2R,3R,5S)-3-pinanyl]-1-propanol obtained in Example 2.

Chiral gas-chromatographic analysis carried out under the same conditions as those of Example 2 shows the presence of two peaks having retention times of 58.67 and 64.80 min.

Odour: earthy note, terpineol, slightly amber-like in the bottom.

EXAMPLE 14

(R/S)-2-Ethyl-3-[(1R,2S,3S,5R)-3-pinanyl]-1-propanol

Under the same conditions as those in Examples 4 and 5, starting from 15.0 g (90 mmol) of (−)-(1R,2R,3R,5S)-3-formylpinane there are obtained 3.3 g of (R/S)-2-ethyl-3-[(1R,2S,3S,5R)-3-pinanyl]-1-propanol (overall yield 16%). IR and $^1$H NMR are identical with the spectra of (R/S)-2-ethyl-3-[(1S,2R,3R,5S)-3-pinanyl]-1-propanol obtained in Example 5. Chiral gas-chromatographic analysis carried out under the same conditions as those of Example 5 shows the presence of two peaks having retention times of 49.85 and 53.65 min. Odour: the bottom develops a slight amber-like note.

EXAMPLE 15

(Z)-2-[4-[(1R,2S,3R,5R)-3-pinanyl]but-3-en-2-yl]-1,3-dioxolane

Under the same conditions as described in Example 8, starting from 10 g (60 mmol) of (−)-(1R,2R,3R,5S)-3-formylpinane there are obtained 8.6 g of (Z)-2-[4-[(1R,2S,3R,5R)-3-pinanyl]but-3-en-2-yl]-1,3-dioxolane (yield=55%). IR and $^1$H NMR are identical with the spectra of (Z)-2-[4-[(1S,2R,3S,5S)-3-pinanyl]but-3-en-2-yl]-1,3-dioxolane (Example 8).

EXAMPLE 16

(E)-2-Methyl-4-[(1R,2S,3R,5R)-3-pinanyl]-2-butenal

Under the same conditions as those of Example 9, starting from 5.0 g (18.9 mmol) of the dioxolane from Example 15 there are obtained 3.3 g of (E)-2-methyl-4-[(1R,2S,3R,5R)-3-pinanyl]-2-butenal (yield=79%).

IR and $^1$H NMR are identical with the spectra of (E)-2-methyl-4-[(1S,2R,3S,5S)-3-pinanyl]-2-butenal (Example 9).

EXAMPLE 17

(E)-2-Methyl-4-[(1R,2S,3R,5R)-3-pinanyl]-2-buten-1-ol

Under the same conditions as those of Example 10, from 1.0 g (45 mmol) of (E)-2-methyl-4-[(1R,2S,3R,5R)-3-pinanyl]2-butenal there is obtained 0.70 g of (E)-2-methyl-4-[(1R,2S,3R,5R)-3-pinanyl]-2-buten-1-ol (yield=70%). IR and $^1$H NMR are identical with the spectra of (E)-2-methyl-4-[(1S,2R,3S,5S)-3-pinanyl]-2-buten-1-ol (Example 10).

Odour: Woody, sandalwood and chalky note, with an amber tendency of ambergris.

EXAMPLE 18

(S)-2-Methyl-3-[(1S,2R,3R,5S)-3-pinanyl]-1-propanol 10 g (47 mmol) of (R/S)-2-methyl-3-[(1S,2R,3R,5S)-3-pinanyl]-1-propanol, prepared in Example 2, are purified by flash chromatography on a column (length 125 cm; diameter 5 cm) containing 1 kg of Matrex 60 Å type silica operating under a pressure of 1.1 bar. After elution with a 95:5 mixture of petroleum ether and ethyl ether and evaporation of the solvents there are isolated 2.4 g of (S)-2-methyl-3-[(1S,2R,3R,5S)-3-pinanyl]-1-propanol (yield 24%). TLC analysis (eluent: petroleum ether: ethyl ether 50:50) shows the presence of a single spot of R$_F$ 0.44.

Gas chromatographic analysis on a Carlo Erba 6000 apparatus fitted with a 50 m column of molten silica attached to a polymethyl-silicone stationary phase operating at a temperature programmed from 70° C. to 240° C. at 2° C./min. shows the presence of a single large peak representing 96.5%.

n$_D^{20}$ 1.4822.

[α]$_D$ = +36.6° (c=2.1, CHCl$_3$).

IR (film): 3330, 2950, 2917, 2902, 2873, 1471, 1454, 1382, 1035 cm$^{-1}$.

$^1$H NMR (200 MHz; CDCl$_3$): 0.74 (d, J=9.4, 1H); 0.96 (d, J=6.5, 3H); 0.99 (s, 3H); 0.99 (d, J=7.0, 3H); 1.0–2.39 (m, 14H); 3.40–3.6 (m, 2H).

$^{13}$C NMR: 67.9(T); 48.4(D); 45.9(T); 44.2(D); 42.0(D); 38.7(S); 35.4(T); 33.9(T); 33.6(D); 33.2(D); 28.1(Q); 23.0(Q); 21.9(Q); 17.9(Q).

Odour: amber-like note, eucalyptus fruit, superb tenacity.

EXAMPLE 19

(S)-2-Ethyl-3-[(1S,2R,3R,5S)-3-pinanyl]-1-propanol 10 g (44 mmol) of (R/S)-2-ethyl-3-[(1S,2R,3R,5S)-3-pinanyl]-1-propanol, prepared in Example 5, are purified by flash chromatography on a column (length 125 cm; diameter 5 cm) containing 1 kg of Matrex 60 Å type silica operating under a pressure of 1.1 bar. After elution with a 95:5 mixture of petroleum ether and ethyl ether and evaporation of the solvents there are isolated 3.7 g of (S)-2-ethyl-3-[(1S,2R,3R,5S)-3-pinanyl]-1-propanol (yield 37%).

TLC analysis (eluent: petroleum ether: ethyl ether 70:30) shows the presence of a single spot of R$_F$ 0.28.

Gas chromatographic analysis on a Carlo Erba 6000 apparatus fitt edwith a 50 m column of molten silica attached to a polymethyl-silicone stationary phase operating at a temperature programmed from 70° C. to 240° C. at 2° C./min. shows the presence of a single large peak representing 96%.

n$_D^{20}$ = 1.4841.

[α]$_D$ = +55.6° (c=2.1, CHCl$_3$).

IR (film): 3333, 2954, 2919, 2903, 2874, 1470, 1456, 1382, 1039 cm$^{-1}$.

$^1$H NMR (200 MHz; CDCl$_3$): 0.74 (d, J=9.4, 1H); 0.91 (t, J=7, 3H); 0.99 (d, J=7, 3H); 0.99~(s, 3H); 1.17 (s, 3H); 1.1–2.4 (m, 13H); 3.57 (m, 2H).

13C NMR: 64.9(T); 48.3(D); 44.3(D); 42.6(T); 42.1(D); 39.4(D); 38.8(S); 35.0(T); 34.2(T); 33.6(D); 28.1(Q); 24.5(T); 23.0(Q); 21.6(Q); 11.3(Q).

Odour: amber-like note, sweet aromatic.

EXAMPLE 20

| Eau de parfum | |
| --- | --- |
| | Parts by weight |
| Artessence Rose; | 10 |
| Coumarin | 20 |
| (R/S)-2-Methyl-3-[(1S,2R,3R,5S)-3-pinanyl]-1-propanol | 20 |
| Vanillin | 20 |
| Jasmin essence; | 30 |
| Ylang eco essence; | 30 |
| Phenylethyl alcohol | 50 |
| Citronellol extra; | 50 |
| Iso E super; IFF | 50 |
| 50% galaxolide (benzyl benzoate) | 70 |
| Irisantheme (alpha-iso-methylionone) | 100 |
| Artessence bergamot; | 150 |
| Magnolione (3-acetonyl-2-pentylcyclopentanone) | 150 |
| Santal super eco essence; | 250 |
| | 1000 |

In this eau de perfume the contribution from compound I modifies the woody, floral and smooth harmony of the bottom notes of the base to confer more volume while developing a fresh oriental side which is very interesting and still smoother.

EXAMPLE 21

| Toilet Water | |
| --- | --- |
| | Parts by weight |
| Essence citron Italia; | 280 |
| Artessence beragmot; | 170 |
| Phixia (hydroxyxitronellal) | 100 |
| Linalyl acetate | 70 |
| Hibiscolide (2,7-dioxocycloeptadecanone) | 60 |
| (R/S)-2-Ethyl-3-[(1S,2R,3R,5S)-3-pinanyl]-1-propanol | 60 |
| Clary sage Oil | 40 |
| Mysore sandalwood oil | 40 |
| Linalool | 30 |
| Amyl salicylate | 30 |
| American Petitgrain oil | 30 |
| Irisantheme (alpha-iso-methylionone) | 30 |
| Geranium oil | 30 |
| Magnolione (3-acetonyl-2-pentylcyclopentanone) | 20 |
| Vetiver oil Java | 10 |
| | 1000 |

In this fresh fougère tobacco harmony the important content of compound I for this harmony type enhances the woody tobacco effect while preserving the top freshness.

We claim:

1. A compound of the formula

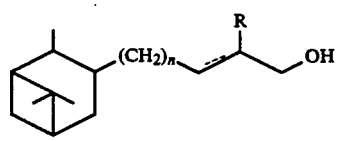

in which R represent H, or $C_1$–$C_4$ alkyl, n represent 0 or 1 and the notation $=\!=$ represents a single or double bond.

2. A compound of formula I according to claim 1, in which R is methyl or ethyl.

3. The compound of claim 1 (R/S)-2-Methyl-3-[(1S,2R,3R,5S)-3-pinanyl]-1-propanol.

4. The compound of claim 1 (E/Z)-2-Methyl-3-[(1S,2R,3S,5S)-3-pinanyl]-2-propen-1-ol.

5. The compound of claim 1 (R/S)-2-Ethyl-3-[(1S,2R,3R,5S)-3-pinanyl]-1-propanol.

6. The compound of claim 1 (E/Z)-2-Ethyl-3-[(1S,2R,3S,5S)-3-pinanyl)-2-propen-1-ol.

7. The compound of claim 1 (E)-2-Methyl-4-[(1S,2R,3S,5S)-3-pinanyl]-2-buten-1-ol.

8. The compound of claim 1 (R/S)-2-Methyl-4-[(1S,2R,3S,5S)-3-pinanyl]-1-butanol.

9. The compound of claim 1 (R/S)-2-Methyl-3-[(1R,2S,3S,5R)-3-pinanyl]-1-propanol.

10. The compound of claim 1 (R/S)-2-Ethyl-3-[(1R,2S,3S,5R)-3-pinanyl]-1-propanol.

11. The compound of claim 1 (E)-2-Methyl-4-[(1R,2S,3R,5R)-3-pinanyl]-2-buten-1-ol.

12. The compound of claim 1 (S)-2-Methyl-3-[(1S,2R,3R,5S)-3-pinanyl]-1-propanol.

13. The compound of claim 1 (S)-2-ethyl-3-[(1S,2R,3R,5S)-3-pinanyl]-1-propanol.

14. An odorant composition having at least two components, one of the components being a compound of the formula

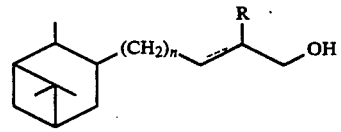

in which R represents H or $C_1$–$C_4$ alkyl and n represents 0 or 1 and the designation $=\!=\!=$ represents a single or double bond.

* * * * *

UNITED STATES PATENT AND TRADEMARK OFFICE
CERTIFICATE OF CORRECTION

PATENT NO. : 5,329,052
DATED : July 12, 1994
INVENTOR(S) : Bernard Auger, et al.

It is certified that error appears in the above-identified patent and that said Letters Patent is hereby corrected as shown below:

On the Title Page, [86], § 371 and § 102(e) dates should read August 5, 1993.

Signed and Sealed this

Eighteenth Day of October, 1994

Attest:

BRUCE LEHMAN

Attesting Officer

Commissioner of Patents and Trademarks